United States Patent
Ganesan

(10) Patent No.: US 8,093,056 B2
(45) Date of Patent: Jan. 10, 2012

(54) METHOD AND APPARATUS FOR ANALYZING A HYDROCARBON MIXTURE USING NUCLEAR MAGNETIC RESONANCE MEASUREMENTS

(75) Inventor: Krishnamurthy Ganesan, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 610 days.

(21) Appl. No.: 11/770,950

(22) Filed: Jun. 29, 2007

(65) Prior Publication Data

US 2009/0004748 A1   Jan. 1, 2009

(51) Int. Cl.
  *G01N 24/08* (2006.01)
  *G01N 24/00* (2006.01)
  *G01N 33/00* (2006.01)
  *G01N 33/24* (2006.01)
  *B01J 19/00* (2006.01)

(52) U.S. Cl. ........... 436/28; 436/139; 436/25; 422/68.1; 422/50; 324/300; 324/303; 324/307; 324/308

(58) Field of Classification Search ............... 436/139, 436/28, 25; 422/68.1, 50; 324/300, 303, 324/307, 308
See application file for complete search history.

(56) References Cited

U.S. PATENT DOCUMENTS

| | | | |
|---|---|---|---|
| 4,866,983 A * | 9/1989 | Vinegar et al. | 73/152.09 |
| 5,739,038 A * | 4/1998 | Burrows | 436/113 |
| 6,046,587 A * | 4/2000 | King et al. | 324/306 |
| 6,229,308 B1 | 5/2001 | Freedman | |
| 6,859,032 B2 | 2/2005 | Heaton et al. | |
| 7,117,100 B2 * | 10/2006 | Venkataraman et al. | 702/27 |
| 7,301,339 B1 * | 11/2007 | Cheng et al. | 324/303 |
| 2003/0040118 A1 * | 2/2003 | Potyrailo et al. | 436/52 |
| 2005/0170516 A1 * | 8/2005 | Kharrat et al. | 436/60 |
| 2005/0221495 A1 * | 10/2005 | Bell et al. | 436/60 |

OTHER PUBLICATIONS

Callaghan and Pinder, "A pulsed field gradient NMR study of self-diffusion in a polydisperse polymer system: dextran in water," *Macromolecules*, 16:968-973, 1983.
Callaghan and Pinder, "Self-diffusion of random-coil polystyrene determined by pulsed field gradient nuclear magnetic resonance: dependence on concentration and molar mass," *Macromolecules*, 14:1334-1340, 1981.
Freedman, Heaton and Flaum, "Field applications of a new nuclear magnetic resonance fluid characterization method," *SPE Reservior & Engineering*, pp. 455-464, Dec. 2002.
Klein and Ries, "The dynamics and physical structure of polymers above the glass transition—transverse relaxation studies of linear chains, star polymers and networks," *Progress in Nuclear Magnetic Resonance Spectroscopy*, 42:31-52, 2003.
Meiboom and Gill, "Modified spin-echo method for measuring nuclear relaxation times," *The Review of Scientific Instruments*, 29(8):688-691, Aug. 1958.

(Continued)

*Primary Examiner* — Christine T Mui
(74) *Attorney, Agent, or Firm* — David J Smith

(57) ABSTRACT

A method and apparatus to determine the fractional amount of at least one constituent of a hydrocarbon mixture, comprising dissolving the hydrocarbon mixture in a substantially hydrogen free solvent to produce a diluted solution, the diluted solution having sufficient solvent to render a NMR property of the diluted solution to be predictably related to the constituent concentrations of the hydrocarbon mixture; making NMR measurements on the diluted solution; and determining the fractional amount of at least one constituent of the hydrocarbon mixture from the NMR measurements.

21 Claims, 3 Drawing Sheets

OTHER PUBLICATIONS

Raghavan, Maver and Blum, "Nuclear magnetic resonance measurements of molecular weights. Self-diffusion of poly(methyl methacrylate) in Acetonitrile," *Macromolecules*, 20:814-818, 1987.

von Meerwall, Amis and Ferry, "Self-diffusion in solutions of polystyrene in tetrahydrofuran: Comparison of concentration dependences of the diffusion coefficients of polymer, solvent, and a ternary probe component," *Macromolecules*, 18:260-266, 1985.

Chen et al., "Determination of molecular weight distribution for polymers by diffusion-ordered NMR," *J. Am. Chem. Soc.*, 117:7965-7970, 1995.

Morris and Johnsons Jr., "Resolution of discrete and continuous molecular size distributions by means of diffusion-ordered 2D NMR spectroscopy," *J. Am. Chem. Soc.*, 115:4291-4299, 1993.

\* cited by examiner

METHOD AND APPARATUS FOR ANALYZING A HYDROCARBON MIXTURE USING NUCLEAR MAGNETIC RESONANCE MEASUREMENTS

CROSS-REFERENCE TO RELATED APPLICATIONS

Not applicable

STATEMENT REGARDING FEDERALLY SPONSORED RESEARCH OR DEVELOPMENT

Not Applicable

BACKGROUND OF THE INVENTION

1. Field of the Invention

The invention relates generally to the field of nuclear magnetic resonance ("NMR") analysis of chemical composition of fluids. More particularly, the invention relates to methods and apparatus for determining molecular weight distribution of hydrocarbons in crude oil using NMR measurements.

2. Background Art

Analysis of liquid phase hydrocarbons ("crude oil") produced from subsurface reservoirs include molecular weight distribution analysis. Such analysis can assist the reservoir operator in determining appropriate extraction techniques to optimize the economic value of the reservoir and to reduce the possibility of premature failure of one or more wellbores used to extract fluids from the reservoir.

Molecular weight distribution analysis can be performed by many different techniques in the laboratory. Such techniques include, for example, liquid chromatography, gas chromatography, and NMR relaxation spectroscopy. NMR relaxation spectroscopy has the advantage has the advantage of not requiring and chemical change to the sample being analyzed. As a result, NMR relaxation spectroscopy is well suited for use both in the laboratory and at the location of the wellbores used to extract the hydrocarbons from the subsurface reservoirs.

A techniques for analyzing molecular weight distribution in crude oil samples is described is U.S. Pat. No. 6,859,032 issued to Heaton et. al. and assigned to the assignee of the present invention. The method disclosed in the '032 publication includes measuring NMR data of the mixture using an NMR tool or a laboratory NMR instrument, deriving at least one parameter for each observed constituent in the mixture from the NMR data, and calculating a molecular property for each observed constituent in the mixture from the at least one parameter. Methods according to some embodiments use correlations between relaxation times and molecular properties and/or between diffusion rates and molecular properties.

It has been observed that certain NMR properties, e.g., transverse relaxation time ($T_2$), and self diffusion constant (D) of hydrocarbons may be related to their relative concentration in a mixture of hydrocarbons. See, R. Freedman, et al., *Field Applications of a New Nuclear Magnetic Resonance Fluid Characterization Method SPE Reservoir Evaluation & Engineering*, 455 (Dec. 2002). The investigation described in the foregoing publication related to mixtures of hexane and squalene and it is believed that the principle suggested therein is applicable to crude oil mixtures of hydrocarbons. What is needed is a method for analyzing mixtures of hydrocarbons using NMR measurements that is relatively insensitive to the relative concentrations of the constituent components.

SUMMARY OF THE INVENTION

A method and apparatus to determine the fractional amount of at least one constituent of a hydrocarbon mixture, comprising dissolving the hydrocarbon mixture in a substantially hydrogen free solvent to produce a diluted solution, the diluted solution having sufficient solvent to render a NMR property of the diluted solution to be predictably related to the constituent concentrations of the hydrocarbon mixture; making NMR measurements on the diluted solution; and determining the fractional amount of at least one constituent of the hydrocarbon mixture from the NMR measurements.

In one example, a molecular weight distribution of the crude oil is determined from the nuclear magnetic resonance measurements.

An apparatus for analyzing a crude oil sample according to another aspect of the invention includes means for mixing a selected amount of crude oil and a solvent, wherein the solvent is substantially hydrogen free. The apparatus includes means for measuring at least one nuclear magnetic resonance property of the mixed crude oil and solvent.

Other aspects and advantages of the invention will be apparent from the following description and the appended claims.

DETAILED DESCRIPTION

Figure 1:
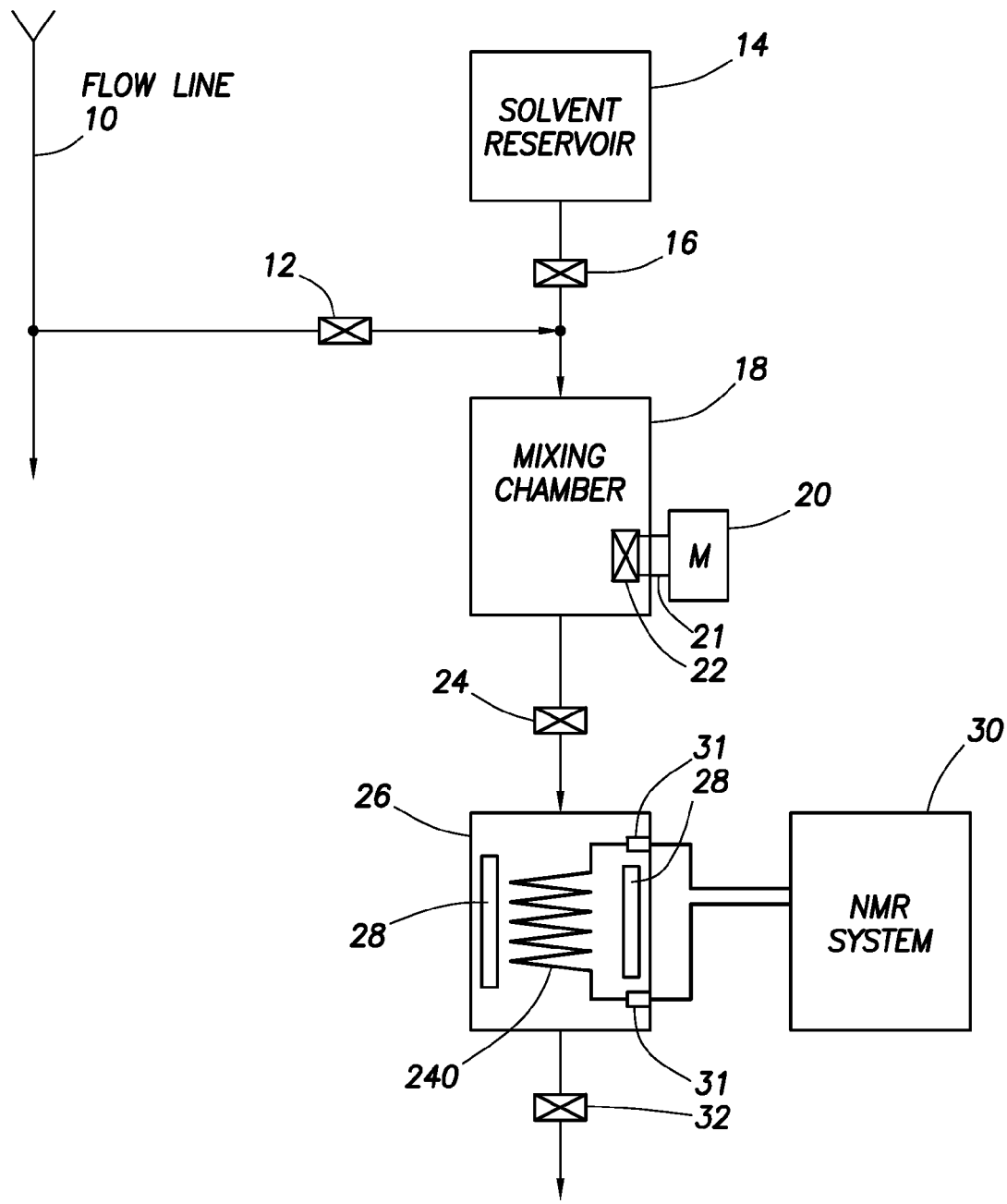
FIG. 1 shows an example apparatus used to make NMR measurements on crude oil samples.

One example of a crude oil analysis apparatus is shown schematically in FIG. 1. The apparatus can include a first valve 12 coupled to a flow line 10. The flow line 10 may be a conduit or pipe coupled to the outlet of a wellbore (not shown) drilled through a subsurface reservoir. The flow line 10 alternatively may be a fluid conduit hydraulically coupled downstream of an oil/water separator (not shown) such that most or all of any produced water is removed from the crude oil to be analyzed when withdrawn from the flow line 10. The first valve 12 may be automatically or manually operated, and when opened can enable a selected amount of crude oil to be discharged into a mixing chamber 18. The mixing chamber 18 may be a pressure resistant tank or similar device to hold a sample of the crude oil. In some examples, the crude oil is held under suitable hydrostatic pressure.

A solvent reservoir 14 holds a suitable solvent for diluting the crude oil sample disposed (or to be disposed) in the mixing chamber 18. Such solvent is preferably a substantially hydrogen free solvent capable of holding in solution all the constituent hydrocarbon components of the crude oil sample. Non-limiting examples of such solvent include, for example, deuterated toluene, chloroform, carbon tetrachloride, hexachlorobenzine, difluorodichlorormethane or any other completely halogenated aliphatic or aromatic hydrocarbon. It is preferred that the solvent be substantially hydrogen free so as to prevent interference with the NMR measurements to be made on the crude oil sample. Such measurements are typically configured to excite and measure NMR phenomena in hydrogen nuclei in the molecules of the crude oil sample. A second valve 16 may be manually or automatically operated in discharge a measured amount of solvent into the mixing chamber 18. It is believed that the selected volume of solvent will be from one to nine times the volume of the crude oil sample discharged into the mixing chamber 18 for purposes of carrying out measurements according to the invention.

It has been determined by several investigators that concentration dependence of certain NMR properties of constituents of hydrocarbon mixtures, e.g., transverse relaxation ($T_2$) and self diffusion (D) may be reduced if the constituent is diluted in a solvent. See, e.g., *Self Diffusion of Random-Coil Polystyrne Determined by Pulsed Field Gradient Nuclear Magnetic Resonance: Dependence on Concentration and Molecular Mass, Macromolecules*, 14, 1334-1340 (1981). See also, E. D. von Meerwall et. al, *Self Diffusion in Solutions of Polystyrene in Tetrahydrofuran: Comparison of Concentration Dependences of the Diffusion Coefficients of Polymer, Solvent and a ternary Probe Component*, Macromolecules, 18, 260 (1985). By sufficiently dissolving the crude oil samples in a solvent that itself is not excited to produce NMR phenomena, it is possible to determine the molecular weight distribution of the crude oil samples more accurately than is possible by analyzing an undiluted sample thereof. The NMR properties of individual constituents of the hydrocarbon mixture are modified by the interaction of the constituents to the extent that assignment of those NMR properties to individual constituents is not trivial. This is also true in highly concentrated solutions of the constituents, but at sufficiently low concentrations this effect becomes negligible. As used herein, "constituent" includes a particular compound or, in a more complicated mixture, a group of compounds.

The relative volumes of solvent and crude oil suggested above are intended to provide analysis results that substantially reduce the sensitivity of the NMR measurements on the relative concentrations of the various constituents of the crude oil sample, while at the same time maintaining sufficient NMR signal amplitude for accurate analysis. It will be appreciated by those skilled in the art that excessive dilution may retain too much concentration dependence of the various constituents on the NMR measurements to provide the benefit of sample dilution on the accuracy of the results.

To insure a sufficient amount of solvent has been added, either of two approaches may be used. In one approach, the solvent may be added successively or incrementally to the sample and NMR measurements made on each successive diluted sample. The NMR property can be monitored and when it is observed that the NMR property is predictably related to the constituent concentrations, no further solvent need be added. An alternative approach is to prepare different concentrations of samples, make NMR measurements on each sample concentration, and determining which samples show the NMR property is predictably related to the constituent concentrations.

The missing chamber 18 may include an agitator to induce complete mixing of the crude oil sample and the solvent. In one example as shown in FIG. 1, the agitator may include a motor 20 rotationally coupled through a magnetic torque transfer coupling 21 to an impeller 22 disposed inside the mixing chamber 18. Other agitating devices will occur to those skilled in the art and may include, for example, a ferromagnetic ball or similar device disposed externally to the missing chamber 18.

An outlet of the mixing chamber 18 may be selectively discharged through a third valve 24 into a measurements chamber 26. The measurement chamber 26 may also be a pressure resistant tank. Preferably the measurement chamber 26 is formed from non-magnetic material. NMR measurement components that may be disposed inside the measurement chamber 26 include a magnet 28, which may be a permanent magnet or electromagnet, and an antenna 240, described in more detail with reference to FIG. 2. The magnet 28 and antenna 240 are configured to enable excitation and measurement of NMR phenomena in the portion of the mixed solvent and crude oil sample disposed within a measurement volume (not shown separately). As will be appreciate by those skilled in the art, the magnet 28 will polarize nuclei along the direction of the static magnetic field induced by the magnet 28. In the example shown in FIG. 1 the magnet 28 may consist of two, side by side, laterally spaced apart plate type magnets having polarization direction transverse to the plane of the plate. The antenna 240 may be a longitudinally wound wire coil. The configuration shown in FIG. 1 polarizes nuclei transversely to the plane of the magnetic plates. Reorientation of the nuclei by the RF magnetic field would thus be along the longitudinal direction of antenna coil. It will be appreciated by those skilled in the art than any other configuration of magnet and antenna may be used to provide that the static magnetic spatial distribution of the magnet is known and within the excitation volume of at least the portion of the antenna whose dipole moment is transverse to the static magnets field direction.

The measurement volume is typically located in the homogeneous field of the magnet 28. As will be appreciated by those skilled in the art, the measurement volume is defined by the spatial distribution of the static magnetic field induced by the magnet 28 and by the frequency and spatial distribution of a radio frequency ("RF") magnetic field induced by passing alternating electrical current through an antenna 240. In some examples, the magnet 28 may be arranged such that a substantially homogeneous static magnetic field volume is defined within the interior space enclosed by the magnet 28, and the frequency and spatial distribution of the RF magnetic field can be selected such that hydrogen nuclei in the crude oil/solvent mixture are excited to produce NMR phenomena in substantially all the volume of such homogeneous static magnetic field. One possible advantage of suing a homogeneous static magnetic field is to maximize the volume of the sample in which the NMR phenomena are excited, thus maximizing the signal to noise ratio of measurements made on the sample. Other examples may include selected gradient magnetic fields superimposed on or associated with the static magnetic field to improve measurements made on the sample related to the self diffusion constant (D).

The antenna 240 may be electrically coupled to an NMR acquisitions system 30 (explained below in more detail with reference to FIG. 2) through the wall of the measurement chamber 28 using pressure sealed electrical feed through the bulkheads 31 of any known type in the art. Configured as shown in FIG. 1, it may be possible to make NMR measurements on the sample in the chamber 28 under selected hydrostatic pressure. Making measurements under such pressure may be necessary when using certain solvents, for example, or to determine the crude oil composition prior to exsolution of low molecular weight components present in the crude oil at reservoir pressure that would take place if the pressure on the sample were substantially reduced.

After NMR measurements are made on a particular sample, the sample may be discharged from the measurement chamber 28 by opening a fourth valve 32. The measurement chamber 28 is thus made ready for a new sample when deemed appropriate.

Figure 2:
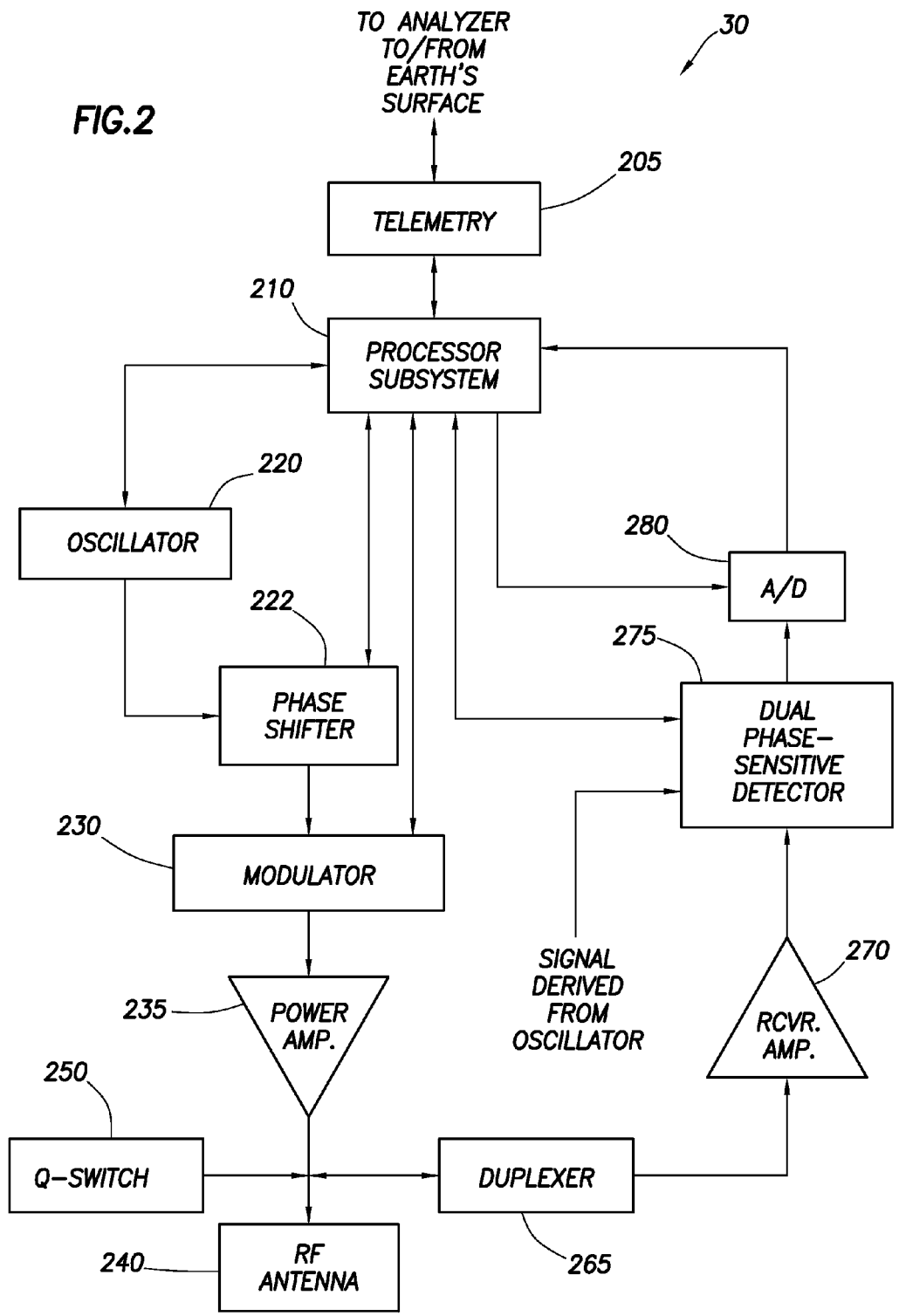
FIG. 2 illustrates a schematic diagram of a circuitry of an NMR measurement system used with the apparatus of FIG. 1 for producing the RF pulses and for receiving and storing spin echoes.

FIG. 2 shows a functional block diagram of the circuitry of the NMR acquisition system 30 for producing the RF pulses and for receiving and storing signals corresponding to spin echoes induced in the nuclei of the crude oil constituent components. Those skilled in the art will appreciate that any other suitable circuitry could be used without departing from the scope of the invention. In FIG. 2, a processor 210 has associated memory, timing, interfaces, and peripherals (not separately shown), of types known in the art to be used with an NMR acquisitions system. The processor 210 can be any microprocessor based device used for system programming and control, and can be coupled with telemetry circuitry 205, for communication with an analyzer (not shown). The pulse forming circuitry includes an oscillator 220 which, under control of processor 210, produces radio frequency (RF) signals at the desired frequency, typically on the order of a few MHz to tens of MHz for use in measuring dilute solutions according to the invention. The output of the oscillator 220 is coupled to a phase shifter 222, the output of which is coupled to a modulator 230, both of which are under the control of processor 210. The pulse shifter 222 and modulator 230 can be controlled, in a manner known in the art, to produce the desired pulses of the RF field, for example the 90 degree and 180 degree pulses for Carr-Purcell-Meiboom-Gill ("CPMG") pulse sequences or any other desired NMR pulse sequences. The output of modulator 230 is coupled to a power amplifier 235, the output of which is coupled to the RF antenna 240. A Q-switch 250 can be provided to damp the RF antenna system to reduce antenna ringing. The antenna 240 is also coupled a receiver section via duplexer 265, the output of which is coupled to a received amplifier 270. The duplexer 265 protects the receiver amplifier 270 from the high power pulses which pass to the RF antenna 240 during the transmitting and damping modes. During the receiving mode, the duplexer 265 acts as a low impedance connection from antenna 240 to the receiver amplifier 270. The output of the receiver amplifier 270 is coupled to a dual phase-sensitive detector 275, which also received, as a reference, a signal derived from the oscillator 220. The detector output is coupled to an analog-to-digital converter 280, the output of which is a digital version of the received nuclear magnetic resonance signals. Although the NMR system 30 is shown as a single body in FIG. 1, it may alternatively comprise separate components.

Several NMR parameters may be measured that can be used to derive fluid properties. Most NMR systems for reservoir evaluation measure the spin-lattice (longitudinal) relaxation times ($T_1$) and/or spin-spin (transverse) relaxation times ($T_2$) of hydrogen nuclei, and self diffusion constants (D). In addition, some NMR systems may provide a ratio of $T_1/T_2$ directly. The foregoing NMR properties are all applicable to the embodiments of the present invention.

Figure 3:
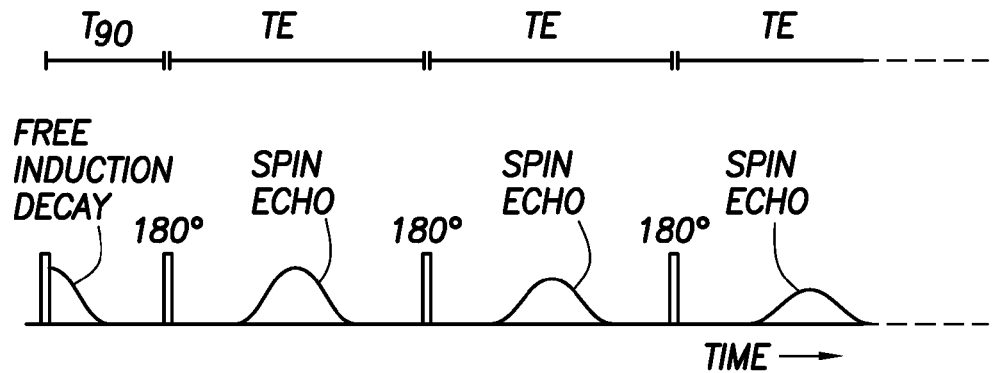
FIG. 3 is a diagram illustrating a common pulse sequence for measuring transverse relaxation times of NMR signals and the resultant spin echoes that can be used to derive transverse relaxation times from nuclear magnetic resonance signals.

Various pulse sequences are available for measuring the NMR relaxation times. For example, $T_1$ relaxation may be measured using an inversion-recovery or a single spin-echo pulse sequence or any of their derivatives. The $T_2$ relaxation is often measured from a train of spin-echoes that are generated with a series of pulses such as the Carr-Purcell-Meiboom-Gill (CPMG) pulse sequence or some variant of this. The CPMG pulse sequence is well known in the art. (See Meiboom, S., Gill, D. 1958, *Modified Spin Echo Method for Measuring Nuclear Relaxation Times*, Review of Scientific Instruments, 29, 688-91). As illustrated in FIG. 3, the CPMG pulse sequence generates a series of spin echoes, wherein the areas under the spin echo curves exponentially decay as a function of time. The exponential decay lifetime is referred to as transverse relaxation time, $T_2$. Thus, $T_2$ measurements can be accomplished by analyzing the amplitudes to spin echoes thus obtained.

As shown in FIG. 3, in a CMPG sequence, the first RF pulse applied to antenna 240 is a 90-degree pulse, which reorients the hydrogen nuclei onto a plane (transverse plane) perpendicular to the static magnetic field produced by the magnet 28. Shortly after the initial 90-degree pulse, a series of 180-degree pulses, (each with a delay time between the successive 180-degree pulses, TE, approximately twice as long as the initial delay between the 90-degree pulse and the first 180-degree pulse) is applied to the antenna 240. Each of these 180-degree pulses results in a spin echo, namely, a growth and subsequent decay of the detected signal mechanisms. During these measurements, the nuclear spins in the transverse plane gradually decrease amplitudes due to spin-spin interaction and other relaxation mechanisms. Consequently, each successive spin-echo has a lower amplitude than that of the preceding one. $T_2$ relaxation time (the transverse relaxation time) information is then derived from the analysis of the exponential decay profile.

Once NMR data are collected, they can be analyzed, for example, with an inversion method to derive the fluid property information. Any inversion method known in the art is suitable. Transverse NMR relaxation in liquid is mainly through dipole-dipole interactions., which are influences by the dynamic properties of the molecules (e.g., diffusion rates and molecular tumbling rates) and the fluids (e.g., viscosity). Thus, NMR data may be used to provide information on the compositions of the fluids and the properties of the constituents (e.g., molecular sizes). Alternatively, one can use calibration curves to relate the concentration of a constituent to its NMR property. The NMR data are converted to a distribution and the components of the distribution are assigned to individual constituents of the mixture. Once the NMR property is assigned to a constituent, the amplitude is used in conjunction with the calibration curve to determine the fractional amount of the constituent.

Thus, NMR data may be used to derive the diffusion rates and relaxation rates of the molecules. Because the molecular diffusion rates and relaxation rates are sensitive to molecular sizes as well as viscosity of the fluids, NMR data may be used to derive information concerning the composition of crude oils in terms of molecular sizes. A suitable technique for obtaining these distributions in mixtures containing both hydrocarbons (and water) is the Magnetic Resonance Fluid (MRF) characterization method as disclosed in U.S. Pat. No. 6,229,308 B1 issued to Freedman, assigned to the assignee of the present invention and incorporated herein by reference.

Figure 4:
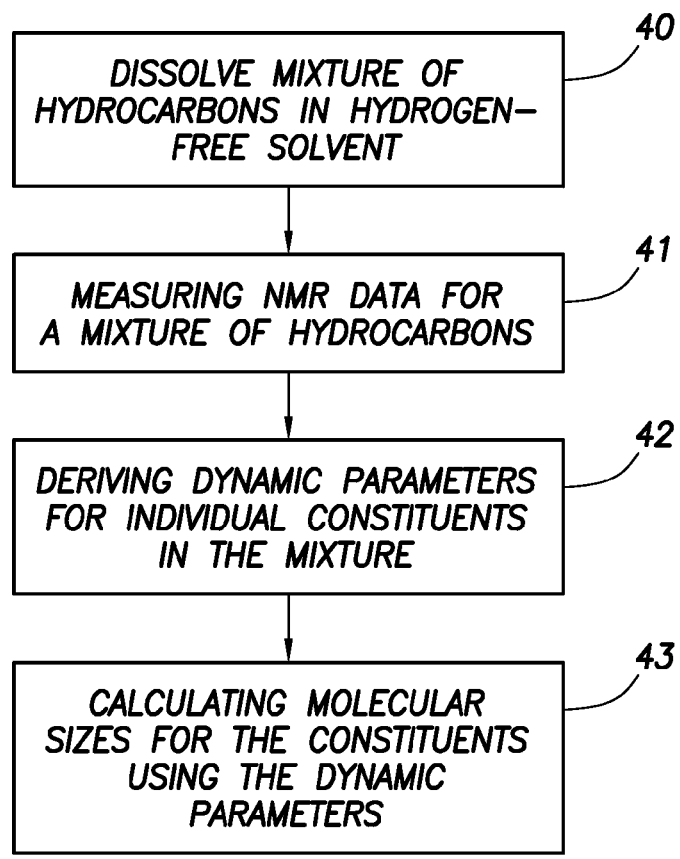
FIG. 4 shows a flow chart of an example method according to the invention.

FIG. 4 summarizes the acts performed in methods for evaluating molecular size distribution in a hydrocarbon mixture according to various examples of the invention. First, the sample of crude oil is dissolved in a hydrogen free solvent as described above, and as shown at 40 in FIG. 4. The NMR data are collected, as shown at 41 in FIG. 4. The foregoing may be performed using the NMR system (30 in FIG. 1).

Once the NMR data are collected, they are analyzed using an inversion method to derive individual constituent dynamic parameters, as shown in FIG. 4. As discussed earlier, the MRF method or any similar method may be used for this purpose. Note that the MRF technique and the extension to it described herein are able to provide real-time information on reservoir fluids.

Finally, the individual constituent dynamic parameters (e.g., $T_1$, $T_2$, $T_1/T_2$, and diffusion constituents) may be used to derive the molecular size information, as shown at 43 in FIG.

4 using an inversion or similar technique. It is to be understood that the invention may include as an analyzed result the molecular weight distribution of all of the various constituent components of a crude oil sample. It is to be clearly understood that for purposes of defining the scope of this invention it is sufficient to determine a fractional amount of at least one constituent in the sample.

Methods and apparatus according to the various aspects of the invention may provide more accurate, rapid analysis of the composition of crude oil samples.

While the invention has been described with respect to a limited member of embodiments, those skilled in the art, having benefit of this disclosure, will appreciate that other embodiments can be devised which do not depart from the scope of the invention as disclosed herein. Accordingly, the scope of the invention should be limited only buy the attached claims.

What is claimed is:

1. A method to determine the fractional amount of at least one constituent hydrocarbon of a hydrocarbon mixture, comprising:
    dissolving the hydrocarbon mixture in a substantially hydrogen free solvent to produce a diluted solution, the diluted solution having sufficient solvent to render a NMR property of the at least one constituent hydrocarbon of the hydrocarbon mixture to be substantially insensitive of the relative concentrations of the other constituent hydrocarbons of the hydrocarbon mixture;
    making NMR measurements on the diluted solution; and
    determining the fractional amount of at least one constituent hydrocarbon of the hydrocarbon mixture from the NMR measurements.

2. The method of claim 1, wherein the NMR measurements comprise measurements related to a longitudinal relaxation time distribution.

3. The method of claim 1, wherein the NMR measurements comprise measurements related to a transverse relaxation time distribution.

4. The method of claim 1, wherein the NMR measurements comprise measurements related to a ratio of longitudinal relaxation time and transverse relaxation time.

5. The method of claim 1, wherein the NMR measurements comprise measurements related to a diffusion constant.

6. The method of claim 1, wherein the solvent comprises a halogenated hydrocarbon.

7. The method of claim 6, wherein the solvent comprises at least one of chloroform, deuterated toluene, and carbon tetrachloride.

8. The method of claim 1, wherein a volume ratio of the solvent to the hydrocarbon mixture is within a range of one-to-one and nine-to-one.

9. The method of claim 1, wherein the dissolving further comprises establishing that sufficient solvent has been added by successively adding an amount of solvent, making the NMR measurements, and monitoring the NMR properties until observing that the NMR property is predictably related to the constituent concentrations.

10. The method of claim 1, further comprising:
    preparing different concentrations of the hydrocarbon mixture to produce a plurality of diluted solutions;
    making the NMR measurements on each diluted solution; and
    determining which samples have sufficient solvent based on the NMR measurements.

11. The method of claim 1, wherein the hydrocarbon mixture is crude oil.

12. The method of claim 1, wherein the method is performed in a wellbore.

13. The method of claim 12, wherein the method is performed in a sampling tool disposed in the wellbore.

14. The method of claim 1, wherein the method is performed on the earth's surface.

15. The method of claim 1, wherein the determining further comprises:
    decomposing the NMR measurements to determine a distribution of the NMR property; and
    assigning a portion of the distribution to a constituent of the hydrocarbon mixture.

16. The method of claim 1, wherein the dissolving and the making NMR measurements are performed at least one of a selected pressure and temperature.

17. The method of claim 1, further comprising determining the molecular weight distribution of the constituents of the hydrocarbon mixture.

18. An apparatus to determine the fractional amount of at least one constituent of a hydrocarbon mixture, comprising:
    a solvent reservoir containing a solvent;
    a source of a hydrocarbon mixture, wherein an amount of the solvent sufficient to dilute the hydrocarbon mixture to render a NMR property of the at least one constituent hydrocarbon of the hydrocarbon mixture to be substantially insensitive of the relative concentrations of the other constituent hydrocarbons of the hydrocarbon mixture;
    a measurement chamber capable of receiving the hydrocarbon mixture and the solvent; and
    a NMR apparatus adjacent to the measurement chamber, wherein the fractional amount of at least one constituent hydrocarbon of the hydrocarbon mixture is determined from a measurement obtained by the NMR apparatus.

19. The apparatus of claim 18, wherein the source of the hydrocarbon mixture is a sampling tool disposed in a wellbore.

20. The apparatus of claim 18, wherein the source of the hydrocarbon mixture is a pipeline.

21. The apparatus of claim 18, wherein the source of the hydrocarbon mixture is a production tubing disposed in a wellbore.

* * * * *